United States Patent [19]

Warriner

[11] Plant 3,997

[45] Dec. 21, 1976

[54] ROSE

[75] Inventor: William A. Warriner, Tustin, Calif.

[73] Assignee: Jackson & Perkins Company, Medford, Oreg.

[21] Appl. No.: 632,762

[22] Filed: Nov. 17, 1975

[51] Int. Cl.[2] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh, Hall & Whinston

CLAIM

A new and distinct cultivar of rose plant of the hybrid tea class, substantially as herein shown and described, characterized particularly as to novelty by the unique combination of its vigorous, well branched growth, an abundance of large, dark green, semi-glossy foliage with blooms of near white with pronounced tinting of Azeala Pink and very little fragrance, and with numerous stipitate glands on the edge and outer surface of sepals on the rachis.

1 Drawing Figure

1

The present invention relates to a new and distinct cultivar of rose plant of the hybrid tea class which was originated by me by crossing the cultivar White Masterpiece, U.S. Plant Pat. No. 2,998 with pollen from the cultivar First Prize, U.S. Plant Pat. No. 2,774.

The primary objective of this breeding was to produce a new rose cultivar in the hybrid tea class with a flower color between the white of White Masterpiece and the pink of First Prize. This objective was substantially achieved along with other desirable improvements as evidenced by the following unique combination of characteristics which are outstanding in the new cultivar and which distinguish it from its parents as well as from all other cultivars of which I am aware:

1. A vigorous, upright plant habit with wide angular lateral branches.
2. An abundance of large, dark green, semi-glossy foliage.
3. Bud and flower color nearly white with a very pronounced irregular area tinted with Azalea Pink.
4. Numerous stipitate glands appearing on the outer surfaces of the sepals and on the rachis.
5. Very little fragrance.

Asexual reproduction of this new cultivar by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed Parent.*—White Masterpiece, U.S. Plant Pat. No. 2,998.

*Pollen Parent.*—First Prize, U.S. Plant Pat. No. 2,774.

Classification:

*Botanical.*—Rosa hybrid.

*Commercial.*—Hybrid tea.

2

FLOWER

Observations made from specimens growth at Irvine, Calif., Sept. 1975.

Blooming habit: Continuous.

Bud:

*Size.*—Approximately 1½" when petals start to unfurl.

*Form.*—Pointed ovoid, broad base.

*Color.*—When sepals first divide near Scarlet (19/1) where first sepal falls, quickly becoming near white. When half blown; upper side of petals near white with a tint of Azalea Pink (618/3) irregularly spread over distal half of petal, lower side of petals near white with a tint lighter than on upper side of petals.

*Sepals.*—Color: Outer surface Scheeles Green (860/3), usually heavily shaded with Garnet Brown (00918), numerous stipitate glands on edges and outer surface. Inner surface Scheeles Green (860/3), occasionally shaded with Garnet Brown (00918), a little white tomentum. Three appendaged sepals lightly appendaged. Two unappendaged sepals hairy edged.

*Receptacle.*—Color: Scheeles Green (860/3) shaded with Garnet Brown (00918). Shape: funnel. Size: large. Surface: smooth.

*Peduncle.*—Length. Medium to short. Surface: Slightly glandular. Color: Bronzy. Strength: Stiff, erect.

*Opening.*—Slow recurving of petals.

Bloom:

*Size.*—Large. Average open size 4½" to 5½".

*Borne.*—Singly or several together.

*Stems.*—Medium, strong.

*Form.*—When first open, high centered. Permanence, retains its form to the end.

*Petalage.*—Number of petals under normal conditions 30–35.

*Color.*—Center of flower: Upper side of petals near white with pronounced tinting of Azalea Pink (618/3). Reverse side of petals near white with less tinting of Azalea Pink (618/3) than upper side of petals. Base of petals near Primrose Yellow (601/1). General tonality from a distance near white with pronounced tinting of petals with Azalea Pink (618/3).

*Discoloration.*—General tonality at end of third or fourth days—After 3–4 days fully open petals are nearly all white with very little Azalea Pink.

*Fragrance.*—Slight.

Petals:

*Texture.*—Thick, leathery.

*Shape.*—Round.

*Form.*—Tips slightly recurved.

*Arrangement.*—Loosely imbricated. Petaloids in center, few.

*Persistence.*—Drop off cleanly.

*Lastingness.*—On the plant—long. As cut flower—long.

Reproductive parts:

*Stamens, anthers.*—Medium. Color—yellow. Arrangement—regular around styles.

*Filaments (threads).*—Color—near Rose Madder (23/1).

*Pollen.*—Lemon yellow.

*Styles.*—Color—Distal half near Rose Madder (23/1), basal half near Primrose Yellow (601/2).

*Stigmas.*—Yellow.

PLANT

Form: Bush.

Growth: Very vigorous, branching, slightly sprawly.

Foliage: Number of leaflets on normal mid-stem leaves, 5, occasionally 7.

*Size.*—Very large to large.

*Quantity.*—Abundant.

*Color.*—New foliage: near Garnet Brown (00918/3). Old foliage: near Parsley Green (00962).

*Shape.*—Oval pointed.

*Texture.*—Upper side—semi-glossy.

*Edge.*—Serrated.

*Serration.*—Single, small.

*Petiole.*—(rachis)—Color—green, reddish markings near the axis. Underside—large prickles. Many stipitate glands on all surfaces of rachis.

*Stipules.*—Long, glandular edged.

*Disease Resistance.*—Resistant to mildew under normal growing conditions at Irvine, Calif.

Wood:

*New Wood.*—Color—Garnet Brown (00918/3). Bark—smooth.

*Old Wood.*—Color—green. Bark, smooth.

Prickles:

*Quantity.*—On main stalks from base—many to ordinary. On laterals from stalk—many to ordinary.

*Form.*—Broad base, medium, hooked downward.

*Color when young.*—Brown.

*Position.*—Irregular.

Small prickles:

*Quantity.*—On main stalks—none. On laterals—none.

I claim:

1. A new and distinct cultivar of rose plant of the hybrid tea class, substantially as herein shown and described, characterized particularly as to novelty by the unique combination of its vigorous, well branched growth, an abundance of large, dark green, semi-glossy foliage with blooms of near white with pronounced tinting of Azeala Pink and very little fragrance, and with numerous stipitate glands on the edge and outer surface of sepals on the rachis.

* * * * *

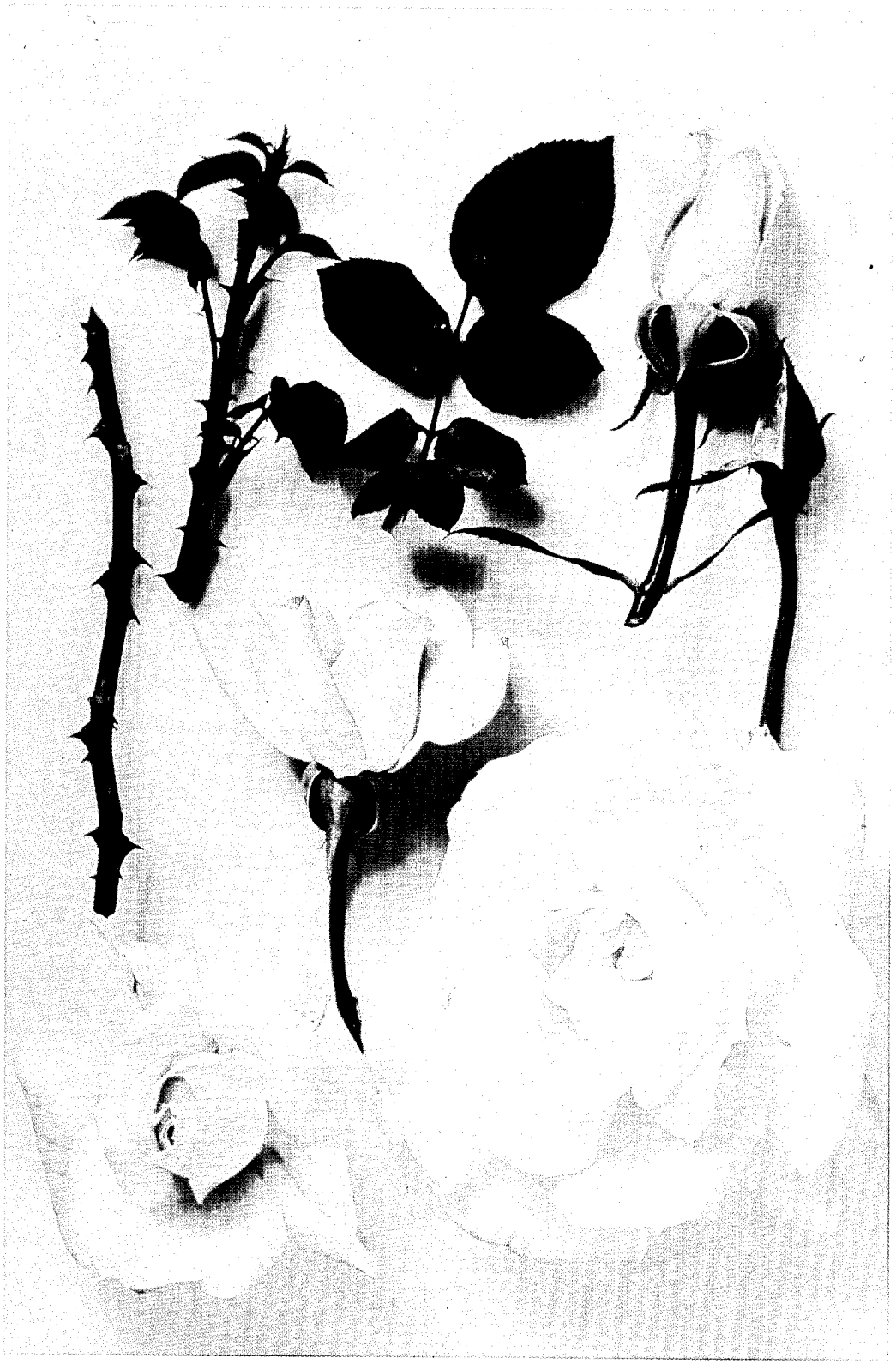

Dec. 21, 1976 W. A. WARRINER Plant Pat. 3,997
ROSE
Filed Nov. 17, 1975